(12) United States Patent
Constantinescu et al.

(10) Patent No.: US 7,741,484 B2
(45) Date of Patent: Jun. 22, 2010

(54) PROCESS FOR SYNTHESIS OF PHENOXY DIAMINOPYRIMIDINE DERIVATIVES

(75) Inventors: Anton Constantinescu, San Mateo, CA (US); Keena Lynn Green, Newark, CA (US); Eric Roy Humphreys, San Bruno, CA (US); Gary R. Lee, Belmont, CA (US); Patrick Finbar McGarry, Colchester, VT (US)

(73) Assignee: Roche Palo Alto LLC, Palo Alto, CA (US)

( * ) Notice: Subject to any disclaimer, the term of this patent is extended or adjusted under 35 U.S.C. 154(b) by 825 days.

(21) Appl. No.: 11/510,208

(22) Filed: Aug. 25, 2006

(65) Prior Publication Data

US 2007/0049751 A1    Mar. 1, 2007

Related U.S. Application Data

(60) Provisional application No. 60/713,280, filed on Sep. 1, 2005.

(51) Int. Cl.
    C07D 239/48    (2006.01)
(52) U.S. Cl. ..................................... 544/298
(58) Field of Classification Search ................. 544/298
    See application file for complete search history.

(56) References Cited

U.S. PATENT DOCUMENTS

2005/0209260 A1    9/2005  Broka et al.

FOREIGN PATENT DOCUMENTS

| WO | WO 00/63183 A | 10/2000 |
| WO | WO 2005/095359 | 10/2005 |

OTHER PUBLICATIONS

Hubig, S.M., et al. "Cation Radicals as Intermediated in Aromatic Halogenation with Iodine Monochloride: Solvent and Salt Effects on the Competition between Chlorination and Iodination," *Journal of Medicinal Chemistry*, 1987 30 (2 ): 6233-6244.

Oberlender, R., et al., "Effect of a Chiral 4-Alkyl Substituent in Hallucinogenic Amphetamines," *Journal of Medicinal Chemistry*, 1995 38 (18): 3593-3601.

Roth, B., et al., "2,4-Diamino-5-benzylpyrimidines as Antibacterial Agents. 7. Analysis of the Effect of 3,5-Dialkyl Substituent Size and Shape on Binding to Four Different Dihydrofolate Reductase Enzymes," *Journal of Organic Chemistry*, 1987 30: 348-356.

*Primary Examiner*—Venkataraman Balasubramanian
(74) *Attorney, Agent, or Firm*—Robert C Hall

(57) ABSTRACT

A method for preparing a compound of formula I

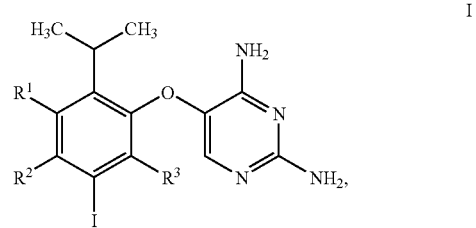

the method comprising treating a compound of formula d

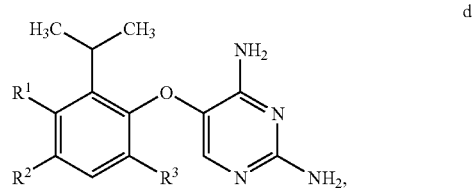

with an iodination reagent, to form the compound of formula I, wherein $R^1$, $R^2$ and $R^3$ are as defined herein.

8 Claims, No Drawings

PROCESS FOR SYNTHESIS OF PHENOXY DIAMINOPYRIMIDINE DERIVATIVES

CROSS REFERENCE TO RELATED APPLICATIONS

This application is entitled to the benefit of provisional patent application Ser. No. 60/713,280 filed on Sep. 1, 2005, the disclosure of which is incorporated herein by reference.

FIELD OF THE INVENTION

This invention pertains to methods of making compounds for treatment of diseases associated with P2X purinergic receptors, and more particularly to methods of using $P2X_3$ and/or $P2X_{2/3}$ antagonists for treatment of genitourinary, gastrointestinal, respiratory, and pain-related diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, $P2X_1$; $P2X_2$; $P2X_3$; $P2X_4$; $P2X_5$; and $P2X_7$; and three heteromeric receptors $P2X_{2/3}$, $P2X_{4/6}$, $P2X_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic $P2X_3$ receptor subunit has also been described (Souslova, et al. (1997) Gene 195:101-111). In vitro, co-expression of $P2X_2$ and $P2X_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). $P2X_3$ receptors have been identified on nociceptive neurons in the tooth pulp (Cook et al., Nature 387:505-508 (1997)). ATP released from damaged cells may thus lead to pain by activating $P2X_3$ and/or $P2X_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that $P2X_2$ and $P2X_3$ are involved in nociception, and that modulators of P2X receptors are potentially useful as analgesics.

Other researchers have shown that $P2X_3$ receptors are expressed in human colon, and are expressed at higher levels in inflamed colon than in normal colon (Y. Yiangou et al, Neuroeastroenterol Mot (2001) 13:365-69). Other researchers have implicated the $P2X_3$ receptor in detection of distension or intraluminal pressure in the intestine, and initiation of reflex contractions (X. Bian et al., J Physiol (2003) 551.1: 309-22), and have linked this to colitis (G. Wynn et al., Am J Physiol Gastrointest Liver Physiol (2004) 287:G647-57); Inge Brouns et al. (Am J Respir Cell Mol Biol (2000) 23:52-61) found that $P2X_3$ receptors are expressed in pulmonary neuroepithelial bodies (NEBs), implicating the receptor in pain transmission in the lung. More recently, others have implicated $P2X_2$ and $P2X_3$ receptors in $pO_2$ detection in pulmonary NEBs (W. Rong et al., J Neurosci (2003) 23(36): 11315-21).

There is accordingly a need for methods of making compounds that are effective modulators of P2X receptors, including the $P2X_3$ and $P2X_{2/3}$ receptors.

SUMMARY OF THE INVENTION

The invention provides a method for preparing a compound of formula I

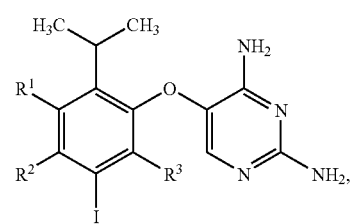

the method comprising:
treating a compound of formula d

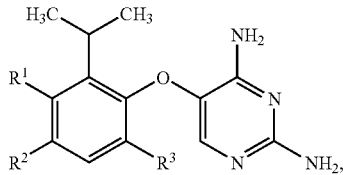

with an iodination reagent, to form the compound of formula I, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; $-(CH_2)_m-(Z)_n-(CO)-R^f$ or $-(CH_2)_m-(Z)_n-SO_2-(NR^g)_n-R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

The method is useful for preparation of compounds that are effective modulators of the $P2X_3$ and $P2X_{2/3}$ receptors. Also disclosed are compounds useful as intermediates in the methods of the invention.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"—R'" where where R' is alkylene, R" is —$SO_2$— and R'" is alkyl as defined herein.

"Alkylamino means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aniline" as used herein refers to compound of the formula Ar—$NH_2$ wherein Ar is aryl or heteroaryl as defined herein. "Aniline" thus encompasses both aryl amines and heteroaryl amines generally wherein the nitrogen atom of the amino group is bound to an aromatic carbon atom. Preferred anilines are aminophenyl compounds. "Aniline" may be optionally substituted as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical -$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Brederick's reagent" as used herein means alkoxyoxybis(dialkylamino)methane wherein the "alkyl" moieties are any lower alkyl and the alkoxy moiety is any lower alkyl. Preferably, "Brederick's reagent" is t-butoxybis(dimethylamino)methane.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Guanidinyl" means a compound of the formula

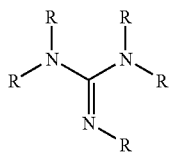

wherein each R independently is hydrogen, alkyl, a leaving group or group easily hydrolizable. R is preferably hydrogen.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Polar aprotic solvent" means a solvent comprised of molecules having polar groups thereon, but without mobile protons. Exemplary polar aprotic solvents include, without limitation, dimethyl formamide, acetonitrile, dimethyl sulfoxide, N,N-dimethyl acetamide, N-methylpyrrolidinone, tetrahydrofuran, dioxane, ethyl acetate, tetrahydropyran, pyridine, acetone, 2-propanone, 2-butanone, ethylene glycol dimethyl ether, methylene chloride, chloroform, and the like.

"Urea" or "ureido" means a group of the formula —NR'—C(O)—NR"R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R''' each independently is hydrogen or alkyl.

"Optionally substituted", when used in association with "aryl", phenyl", "heteroaryl" "cycloalkyl", "heterocyclyl", or "aniline" means an aryl, phenyl, heteroaryl, cyclohexyl, heterocyclyl or aniline which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl(carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solution" as used herein is meant to encompass liquids wherein a reagent or reactant is present in a solvent in dissolved form (as a solute) or is present in particulate, undissolved form, or both. Thus, in a "solution", it is contemplated that the solute may not be entirely dissolved therein and solid solute may be present in dispersion or slurry form. Accordingly, a "solution" of a particular reagent or reactant is meant to encompasses slurries and dispersions, as well as solutions, of such reagents or reactants. "Solution" and "Slurry" may be used interchangeable herein.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" or "respiratory disease" refers to, without limitation, chronic obstructive pulmonary disease (COPD), asthma, bronchospasm, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center is present in a structure but no specific stereochemistry is shown, both stereoisomers associated with the chiral center are encompassed by the structure.

Methods

U.S. patent application Ser. No. 11/071,555, filed on Mar. 3, 2005, published as US2005/0209260 and incorporated herein by reference, discloses compounds effective modulators of the $P2X_3$ and $P2X_{2/3}$ receptors and uses of these compounds for treatment of $P2X_3$ and/or $P2X_{2/3}$ receptor-mediated diseases. This invention provides methods useful for preparing such compounds, and chemical intermediates useful in such methods.

The methods of the invention will be more fully understood by first referring to Scheme A below, wherein X is halo, Y is halo, tosyl or other leaving group, and Ar, $R^1$, $R^2$, $R^3$ and $R^4$ are as defined herein.

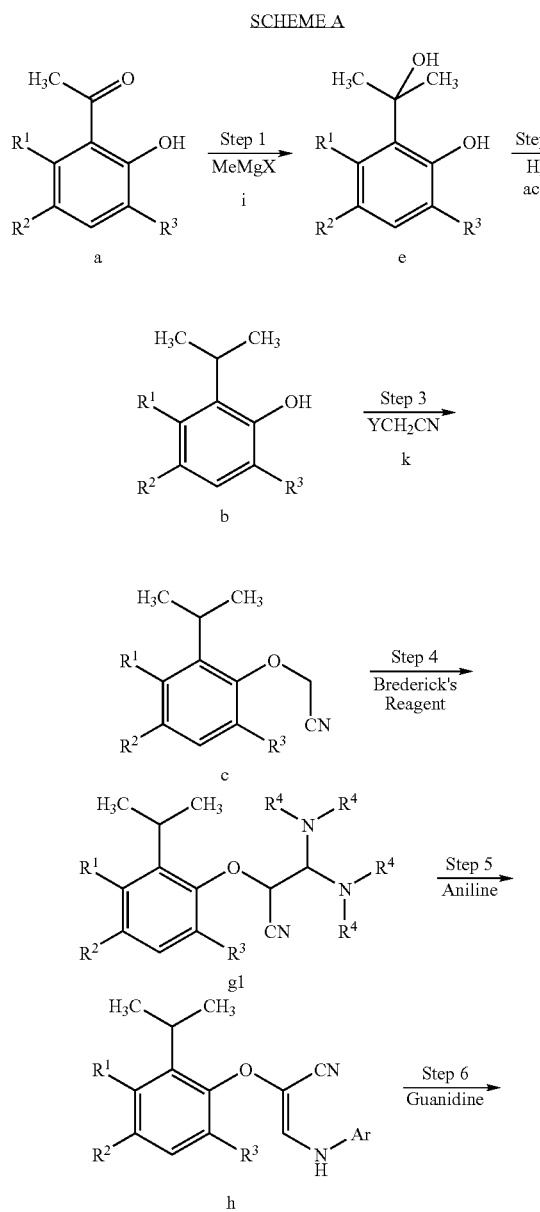

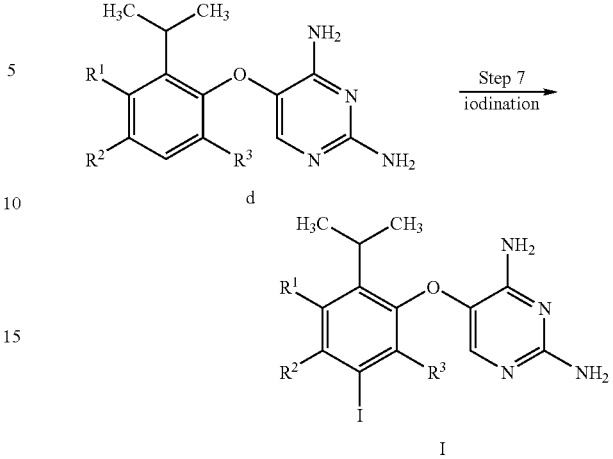

In step 1 of scheme A, acetophenone compound a is treated with a methyl Grignard reagent j, such as methyl magnesium chloride or methyl magnesium bromide, to form tertiary alcohol compound e. This reaction may be carried out, for example, under polar aprotic solvent conditions, such as in solution with THF (tetrahydrofuran), under ambient temperature conditions. Numerous acetophenone compounds a usable with the invention may be prepared by acylation of substituted phenyl compounds or by conventional techniques well known in the art.

In step 2, compound e is subject to hydrogenation to form isopropyl phenol compound b. The hydrogenation reaction of step 2 may be carried out under hydrogen atmosphere under acidic conditions in the presence of a palladium catalyst or other suitable hydrogenation catalyst. The hydrogenation of step 2 may be carried out, for example, under ambient pressure hydrogen atmosphere in polar aprotic solvent such as THF in the presence of HCl.

In many embodiments of the invention, the hydrogenation of step 2 may be carried out without requiring isolation of the as the Grignard reaction product b of step 1. In certain embodiments tertiary alcohol compound e may require isolation, and/or may a separate dehydration reaction wherein an isopropenyl compound (not shown) is formed prior to the hydrogenation of step 2.

In step 3, phenol compound b is treated with a cyanomethyl alkylating agent k to form nitrile ether compound c. Cyanomethyl alkylating agent k may be, for example, toluene-4-sulfonic acid cyanomethyl ester, bromoacetonitrile, chloroacetonitrile, or like alkylating agent. The alkylation of step 3 may be carried out under polar aprotic solvent conditions and in the presence of mild base such as potassium carbonate. In one embodiment the reaction of cyanomethyl alkylating agent k with phenol b may be carried out as a slurry of cyanomethyl alkylating agent k, phenol b and potassium carbonate in a ketone solvent such as 2-butanone, acetone, methyl ethyl ketone, or the like.

Cyanomethyl ether compound c is treated with Brederick's reagent in step 4, to form an aminal compound g1. This reaction may be carried out in a dimethylformamide (DMF) solution or solution of other suitable polar aprotic solvent. "Brederick's reagent" as used herein means (alkoxybis(dialkylamino)methane) generally, wherein the "alkyl" moiety is lower alkyl and the alkoxy moiety is lower alkoxy. In many embodiments the alkyl moiety is methyl, and the alkoxy moiety is tert-butoxy (i.e, "Brederick's reagent" is t-butoxybis(dimethylamino)methane).

In many embodiments aminal compound g1 while in solution exists in equilibrium with cyano enamine g2 as shown below.

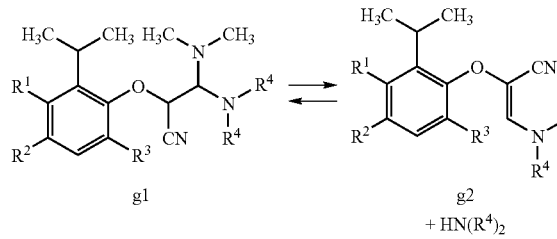

In many embodiments aminal compound g1 is not isolatable as a solid, but instead may be isolated in the form of cyano enamine compound g2. As will be seen below, step 5 may be carried out directly without requiring isolation of compound g1 or g2.

In step 5, aminal compound g1 (or compound g2 or a mixture of compounds g1 and g2) is reacted with an aniline reagent to yield aniline enamine compound h. The aniline reagent used in step 5 may comprise, for example, a compound of the formula Ar—$NH_2$ wherein Ar is optionally substituted aryl or optionally substituted heteroaryl as defined herein. The aniline reagent is preferably in salt form, such as the hydrochloride salt or other stable salt of the corresponding aniline free base. In many embodiments the aniline reagent is a hydrochloride salt of a phenylamine of the formula:

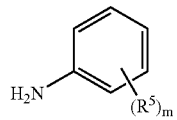

wherein m is from 0 to 4 and $R^5$ is any substituent group compatible with the solvent and reaction conditions of step 5. Preferably m is 0. The reaction of step 5 may be carried out under polar aprotic solvent conditions such as are offered by DMF. In many embodiments the aniline enamine compound h need not be isolated, and step 6 below may be carried out directly while aniline enamine h remains in solution.

In step 6, aniline ether compound h is treated with a guanidine reagent to afford diaminopyrimidine d. The guanidine reagent may comprise guanidine carbonate or other stable salt of guanidine. The reaction of step 6 may be carried out in polar aprotic solvent such as DMF, and in many embodiments may be carried out in the same reaction vessel as steps 4 and 5 as noted above.

In step 7, diaminopyrimidine compound d is subject to iodination to form iodo compound I. Iodination reagents such as iodine monochloride, N-iodosuccinimide or iodine in the presence of an oxidant such a peracid or periodate, may be used in step 7. In many embodiments iodine monochloride may be used under acidic aqueous solvent conditions such acetic acid or a mixture of acetic acid and water.

Scheme B below illustrates another method of the invention wherein X is halo, Y is halo, tosyl or other leaving group, and m, $R^1$, $R^2$, and $R^3$ are as defined herein. In Scheme B, steps 1 and 2 of Scheme A are carried out in the same reaction vessel, and steps 4, 5 and 6 of Scheme A are carried out in the same reaction vessel, without isolation of the corresponding intermediates.

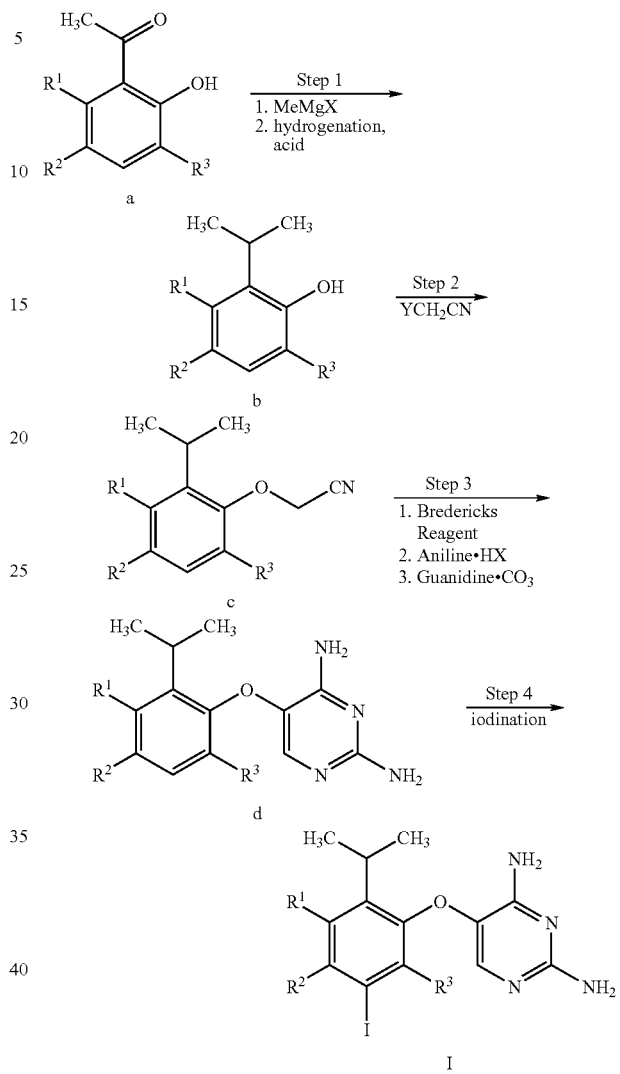

In step 1 of scheme B, acetophenone compound a is treated first with a methyl Grignard reagent j in the manner described above, followed by treatment with hydrogen gas in the presence of suitable catalyst, to afford isopropyl phenol compound b. The Grignard and hydrogenation reactions of step 1 may be carried out in THF or like suitable polar aprotic solvent as noted above.

In step 2, phenol compound b is treated with a cyanomethyl alkylating agent k such as oluene-4-sulfonic acid cyanomethyl ester, to yield a nitrile ether compound c. This reaction may be carried out in a polar aprotic solvent such as a ketone solvent, in the presence of potassium carbonate as noted above.

In step 3, cyano ether c is treated with Bredereck's reagent (t-butoxybis(dimethylamino)methane), followed by an aniline reagent, followed by a guanidine reagent, to directly provide diamino pyrimidine compound d. The reactions of step 3 may all be carried out in DMF or other suitable solvent in a single reaction vessel. As noted above, the aniline reagent is preferably an aniline salt such as aniline hydrochloride, and the guanidine reagent is preferably a guanidine salt such as guanidine carbonate.

In step 4, diamino pyrimidine d is iodinated as described above in Scheme A to yield iodo compound I.

Accordingly, the invention provides a method for preparing a compound of formula I

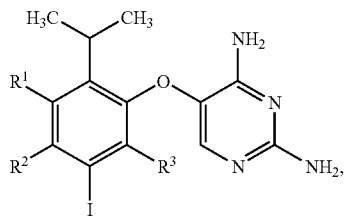

the method comprising:
treating a compound of formula d

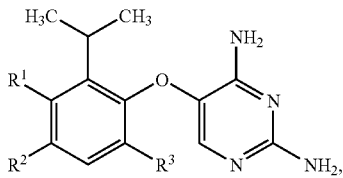

with an iodination reagent, to form the compound of formula I, wherein:

$R^1$, $R^2$ and $R^3$ each independently is: hydrogen; alkyl; alkenyl; alkynyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments the iodination reagent may be iodine monochloride.

In certain embodiments the compound of formula d may be dissolved or partly dissolved in acetic acid or a mixture of acetic acid and water.

In certain embodiments the method may further comprise treating a compound of formula c

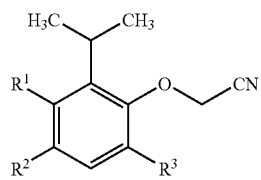

wherein Ar, $R^1$, $R^2$ and $R^3$ are as defined herein, with Brederick's reagent, followed by an aniline, followed by a guanidine, to form the compound of formula d.

In certain embodiments the method may further comprise treating a compound of formula b

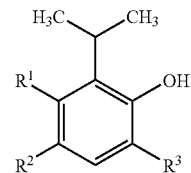

wherein Ar, $R^1$, $R^2$ and $R^3$ are as defined herein, with cyanomethyl alkylating agent, to form the compound of formula c.

In certain embodiments the method may further comprise treating a compound of formula a

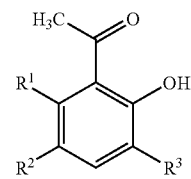

wherein Ar, $R^1$, $R^2$ and $R^3$ are as defined herein, with methylmagnesium halide, followed by hydrogen in the presence of a hydrogenation catalyst and acid, to form said compound of formula b.

In certain embodiments of the subject method, $R^1$ and $R^3$ are hydrogen and $R^2$ is alkoxy, halo or alkynyl.

In certain embodiments of the subject method, $R^2$ and $R^3$ are hydrogen and $R^1$ is alkoxy, halo or alkynyl.

In certain embodiments the method may further comprise treating a compound of formula h

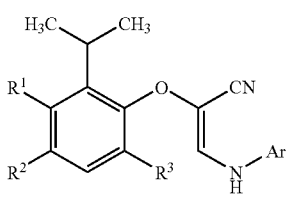

wherein Ar, $R^1$, $R^2$ and $R^3$ are as defined herein, with a guanidine reagent, to form the compound of formula d.

In certain embodiments the guanidine reagent may be guanidine carbonate.

In certain embodiments the method may further comprise treating a compound of formula g1, formula g2, or a mixture thereof,

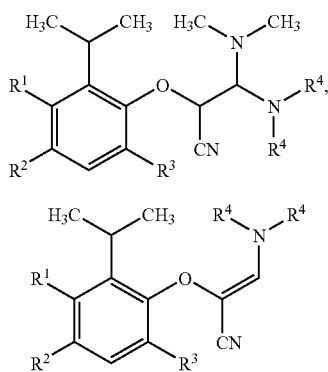

wherein Ar, $R^1$, $R^2$, $R^3$ and $R^4$ are as defined herein, with an aniline reagent, to form the compound of formula h.

In certain embodiments the method may further comprise treating a compound of formula c

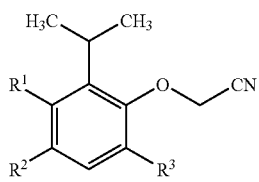

wherein Ar, $R^1$, $R^2$ and $R^3$ are as defined herein, with Brederick's reagent, to form said compound of formula g1, or formula g2, or a mixture thereof.

In other embodiments of the invention, there is provided a method for preparing a compound of formula I

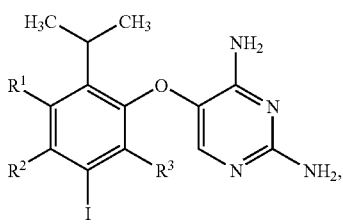

the method comprising:
contacting a solution of a compound of formula d

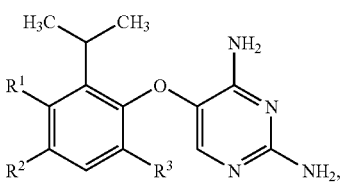

in acetic acid, with iodine monochloride, followed by optional addition of water, to form said compound of formula I, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments the method may further comprise contacting a solution of compound of formula c

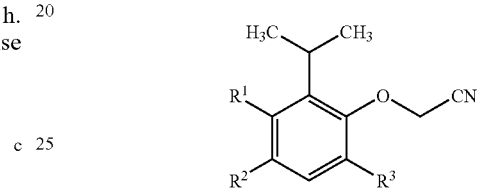

wherein Ar, $R^1$, $R^2$ and $R^3$ are as defined herein, in a polar aprotic solvent, with t-butoxybis(dimethylamino)methane, followed by an aniline salt, followed by a guanidine salt, to form the compound of formula d.

In certain embodiments the method may further comprise contacting a solution of a compound of formula b

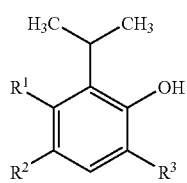

wherein Ar, $R^1$, $R^2$ and $R^3$ are as defined herein, in a polar aprotic solvent, with toluene-4-sulfonic acid cyanomethyl ester, to form the compound of formula c.

In certain embodiments the method may further comprise contacting a solution of a compound of formula a

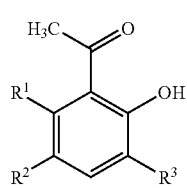

wherein Ar, $R^1$, $R^2$ and $R^3$ are as defined herein, in a polar aprotic solvent, with methylmagnesium halide, followed by hydrogen in the presence of a hydrogenation catalyst and acid, to form the compound of formula b.

The invention also provides compounds of formula d

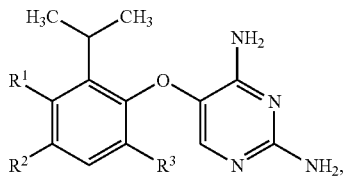

or salts thereof, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N;

provided that when $R^1$ and $R^3$ are hydrogen, $R^2$ is not methoxy.

In certain embodiments of formula d, $R^1$ and $R^3$ are hydrogen and $R^2$ is alkoxy, halo or alkynyl.

In certain embodiments of formula d, $R^2$ and $R^3$ are hydrogen and $R^1$ is alkoxy, halo or alkynyl.

The invention also provides compounds of formula h

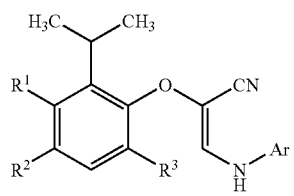

or salts thereof, wherein:

Ar is optionally substituted aryl or optionally substituted heteroaryl; and $R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments of formula h, $R^1$ and $R^3$ are hydrogen and $R^2$ is alkoxy, halo or alkynyl.

In certain embodiments of formula h, $R^2$ and $R^3$ are hydrogen and $R^1$ is alkoxy, halo or alkynyl.

The invention also provides compounds of formula h1

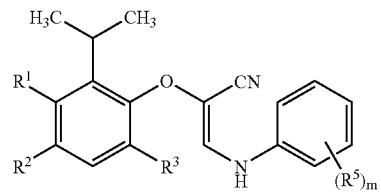

or salts thereof, wherein:

m is from 0 to 4;

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N; and each $R^5$ is independently alkyl, alkoxy, halo, or haloalkyl.

In certain embodiments of formula h1, m is 0, $R^1$ and $R^3$ are hydrogen and $R^2$ is alkoxy, halo or alkynyl. Preferably $R^2$ is alkoxy.

In certain embodiments of formula h1, m is 0, $R^2$ and $R^3$ are hydrogen and $R^1$ is alkoxy, halo or alkynyl. Preferably $R^1$ is alkoxy.

The invention also provides a composition comprising a compound of formula g1

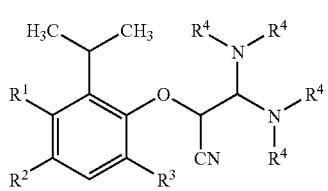

or a salt thereof, in admixture with a polar aprotic solvent, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N; and $R^4$ is alkyl.

In certain embodiments of formula g1, $R^1$ and $R^3$ are hydrogen and $R^2$ is alkoxy, halo or alkynyl. Preferably $R^2$ is alkoxy.

In certain embodiments of formula g1, $R^2$ and $R^3$ are hydrogen and $R^1$ is alkoxy, halo or alkynyl. Preferably $R^1$ is alkoxy.

In certain embodiments of formula g1, $R^4$ is methyl.

The invention also provides compounds of formula g2

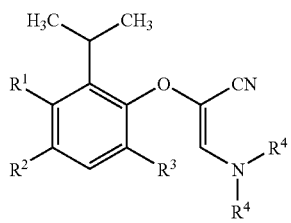

or salts thereof, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N; and $R^4$ is alkyl.

In certain embodiments of formula g2, $R^1$ and $R^3$ are hydrogen and $R^2$ is alkoxy, halo or alkynyl. Preferably $R^2$ is alkoxy.

In certain embodiments of formula g2, $R^2$ and $R^3$ are hydrogen and $R^1$ is alkoxy, halo or alkynyl. Preferably $R^1$ is alkoxy.

In certain embodiments of formula g2, $R^4$ is methyl.

The invention also provides a composition comprising a compound of formula g1, a compound of formula g2, or a mixture thereof,

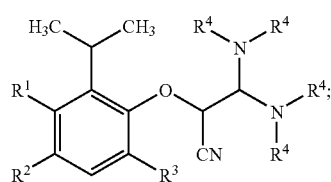

-continued

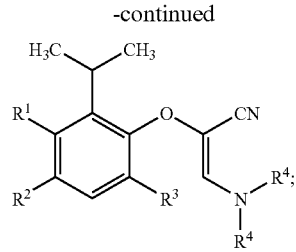

or salts thereof, in admixture with a polar aprotic solvent, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N; and $R^4$ is alkyl.

In certain embodiments of formulas g1 and g2, $R^1$ and $R^3$ are hydrogen and $R^2$ is alkoxy, halo or alkynyl. Preferably $R^2$ is alkoxy.

In certain embodiments of formulas g1 and g2, $R^2$ and $R^3$ are hydrogen and $R^1$ is alkoxy, halo or alkynyl. Preferably $R^1$ is alkoxy.

In certain embodiments of formulas g1 and g2, $R^4$ is methyl.

The invention also provides compounds of formula c

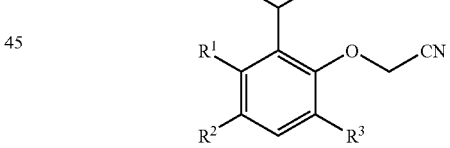

or salts thereof, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments of formula c, $R^1$ and $R^3$ are hydrogen and $R^2$ is alkoxy, halo or alkynyl. Preferably $R^2$ is alkoxy. In certain embodiments of formula c, $R^2$ and $R^3$ are hydrogen and $R^1$ is alkoxy, halo or alkynyl. Preferably R1 is alkoxy.

Scheme C below illustrates another method of the invention wherein X is halo, Y is halo, tosyl or other leaving group, and $R^1$, $R^2$, and $R^3$ are as defined herein.

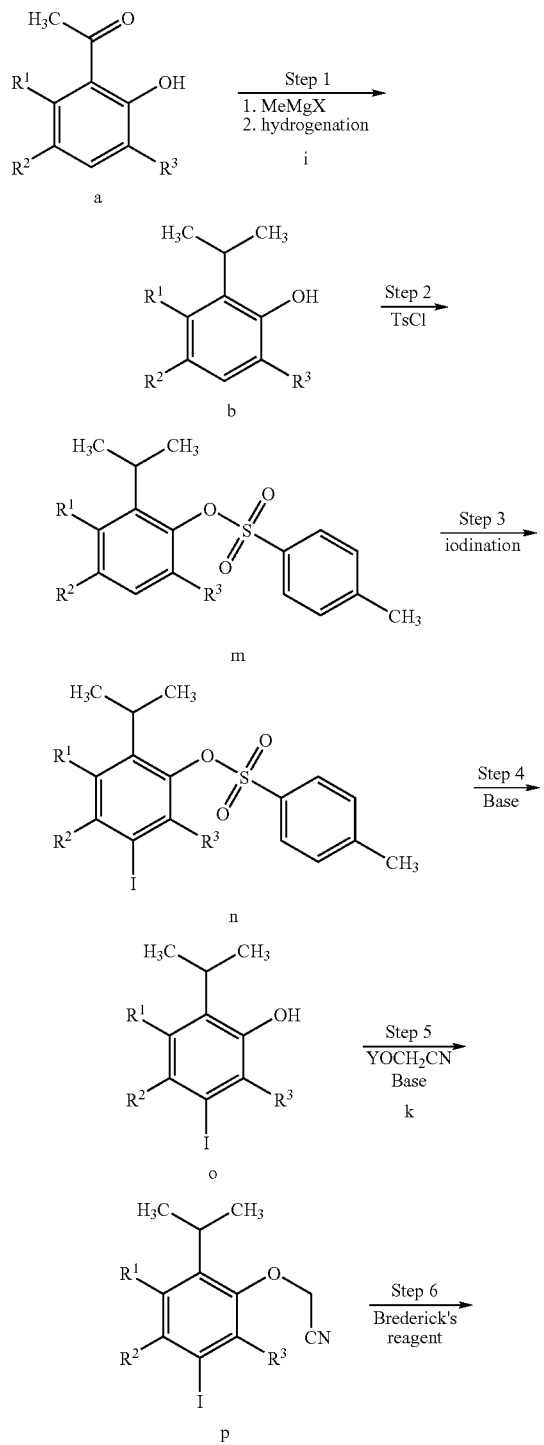

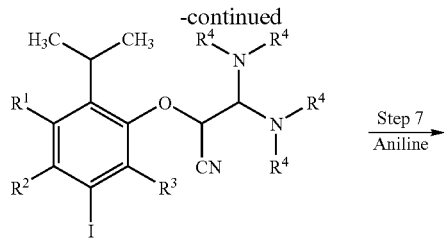

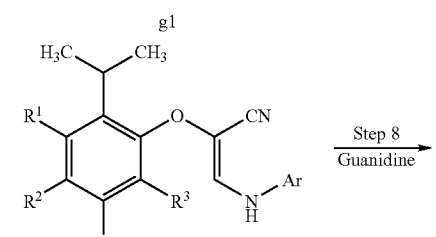

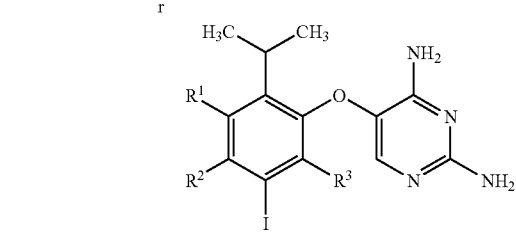

In step 1 of Scheme C, acetophenone compound a is treated first with a methyl Grignard reagent j, followed by treatment with hydrogen gas in the presence of suitable catalyst and under acidic conditions (such as the presence of HCl or other mineral acid), to afford isopropyl phenol compound b in the manner described above.

In step 2, phenol compound b is treated with tosyl chloride to form tosylate compound m. This reaction may be carried out under nonpolar solvent conditions.

An iodination reaction occurs in step 3 wherein tosylate compound m is treated an iodinating reagent to form iodo tosylate compound n. Iodination reagents such as iodine monochloride, N-iodosuccinimide or iodine in the presence of oxidant, may be used in step 3.

In step 4, iodo tosylate is hydrolized to yield iodo phenol compound o. The reaction of step 4 may be carried out under polar protic solvent conditions, such as in an alcohol solvent, in the presence of base such as KOH or NaOH.

In step 5, iodo phenol compound o is treated with a cyanomethyl alkylating agent k to form cyanomethyl ether compound p. Cyanomethyl alkylating agent k may be, for example, toluene-4-sulfonic acid cyanomethyl ester, bromoacetonitrile, chloroacetonitrile, or like alkylating agent as noted above. The reaction of step 5 may be carried out under polar aprotic solvent conditions and in the presence of mild base such as potassium carbonate.

Cyanomethyl ether compound p is treated with Brederick's reagent (alkoxybis(alkylamino)methane) in step 6, to form an aminal compound q1. This reaction may be carried out in a dimethylformamide (DMF) solution or solution of other suitable polar aprotic solvent. As in the case of compounds g1 and g2 discussed above, minal compound q1 while in solution exists in equilibrium with cyano enamine q2 shown below.

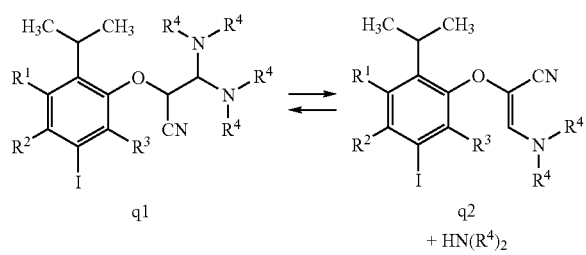

In certain embodiments aminal compound q1 may not isolatable as a solid, but instead may be isolated in the form of cyano enaime compound q2. As in case of the method of Scheme A described above, in many embodiments it is not necessary to isolate compound q1 or q2, and these compounds can remain in solution while step 6 below is carried out.

In step 7, aminal compound q1 (or compound q2 or a mixture of compounds q1 and q2) is reacted with an aniline reagent to yield aniline enamine compound r. The aniline reagent may be an aryl amine or heteroaryl amine as noted above, preferably a phenyl amine. The aniline reagent of step 7 may be in the form of a hydrochloride salt or other stable salt. Again, in many embodiments of the invention the aniline ether compound r need not be isolated, and step 8 below may be carried out while aniline enamine compound r remains in solution.

In step 8, aniline enamine compound r is treated with a guanidine reagent to afford diaminopyrimidine I. The guanidine reagent may comprise guanidine carbonate or other stable salt of guanidine, and the reaction may be carried out under polar aprotic solvent conditions.

Accordingly, the invention provides a method for preparing a compound of formula I

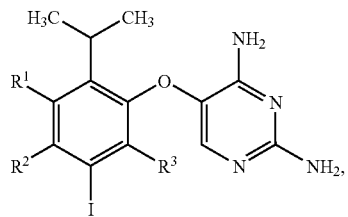

the method comprising:
treating a compound of formula r

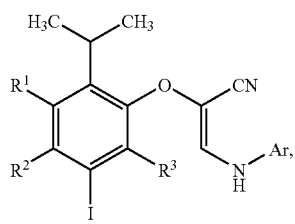

with a guanidine reagent, to form the compound of formula I, wherein:
$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments the guanidine reagent is a guanidine salt such as guanidine carbonate.

In certain embodiments the above method may further comprise treating a compound of formula p

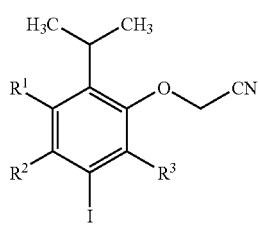

wherein $R^1$, $R^2$ and $R^3$ are as defined herein, with Brederick's reagent, followed by an aniline reagent, to form the compound of formula r.

In certain embodiments the method may further comprise treating a compound of formula q1, q2, or a mixture thereof,

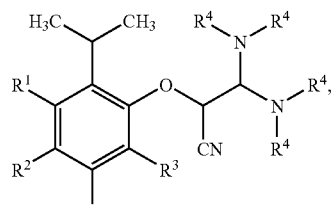

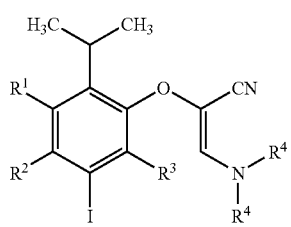

wherein $R^1$, $R^2$, $R^3$ and $R^4$ are as defined herein, with an aniline reagent, to form the compound of formula r.

In certain embodiments the method may further comprise treating a compound of formula o

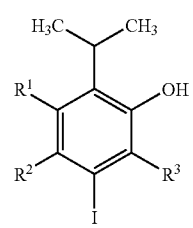

wherein $R^1$, $R^2$ and $R^3$ are as defined herein, with cyanomethyl alkylating agent, to form the compound of formula p.

In another embodiment the invention provides a method for preparing a compound of formula I

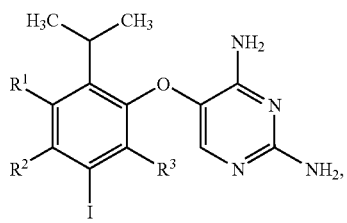

the method comprising:
contacting a solution of a compound of formula r

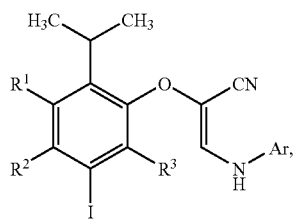

wherein Ar, $R^1$, $R^2$ and $R^3$ are as defined herein, in a polar aprotic solvent, with a guanidine salt, to form the compound of formula I, wherein:

$R^1$, $R^2$ and $R^3$ each independently is: hydrogen; alkyl; alkenyl; alkynyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments the above method may further comprise contacting a solution of a compound of formula p

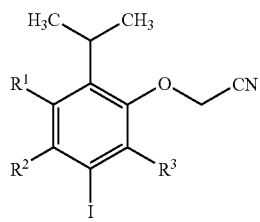

wherein $R^1$, $R^2$ and $R^3$ are as defined herein, in a polar aprotic solvent, with t-butoxybis(dimethylamino) methane, followed by an aniline reagent, to form the compound of formula r.

In certain embodiments the method may further comprise contacting a solution of a compound of formula q1, q2, or a mixture thereof

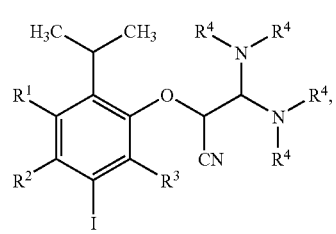

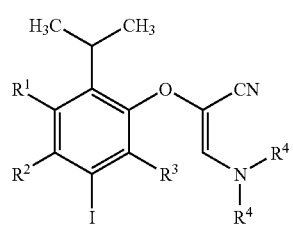

wherein $R^1$, $R^2$, $R^3$ and $R^4$ are as defined herein, in a polar aprotic solvent, with an aniline salt, to form the compound of formula r.

In certain embodiments the method may further comprise contacting a solution of a compound of formula o

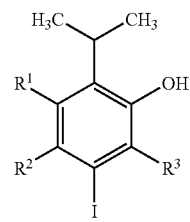

wherein $R^1$, $R^2$ and $R^3$ are as defined herein, in a polar aprotic solvent in the optional presence of base, with cyanomethyl alkylating agent, to form the compound of formula p.

The invention also provides compounds of formula r

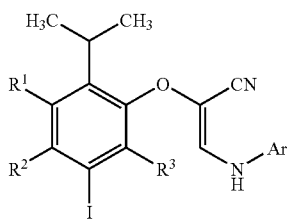

or salts thereof,
wherein:
Ar is optionally substituted aryl or optionally substituted heteroaryl; and $R^1$, $R^2$ and $R^3$ each independently is: hydrogen; alkyl; alkenyl; alkynyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy;

aryloxy; heteroaryloxy; aralkyloxy; heteroaralkyloxy; optionally substituted phenoxy; —(CH$_2$)$_m$—(Z)$_n$—(CO)—R$^f$ or —(CH$_2$)$_m$—(Z)$_n$—SO$_2$—(NR$^g$)$_n$—R$^f$ where m and n each independently is 0 or 1, Z is O or NR$^1$, R$^f$ is hydrogen, alkyl, hydroxy, alkoxy, amino, hydroxyalkyl or alkoxyalkyl, and each R$^g$ is independently hydrogen or alkyl; or R$^2$ and R together with the atoms to which they are attached may form a five or six-membered ring that optionally includes one or two heteroatoms selected from O, S and N.

In certain embodiments of formula r, m is 0, R$^1$ and R$^3$ are hydrogen and R$^2$ is alkoxy, halo or alkynyl. Preferably R$^2$ is alkoxy.

In certain embodiments of formula r, m is 0, R$^2$ and R$^3$ are hydrogen and R$^1$ is alkoxy, halo or alkynyl. Preferably R$^1$ is alkoxy.

The invention also provides a composition comprising a compound of formula q1

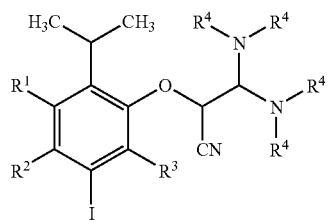

or a salt thereof, in admixture with a polar aprotic solvent, wherein:

R$^1$, R$^2$ and R$^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH$_2$)$_m$—(Z)$_n$—(CO)—R$^f$ or —(CH$_2$)$_m$—(Z)$_n$—SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or R$^2$ and R$^3$ together with the atoms to which they are attached may form a five or six-membered ring that optionally includes one or two heteroatoms selected from O, S and N; and R$^4$ is alkyl.

In certain embodiments of formula q1, R$^1$ and R$^3$ are hydrogen and R$^2$ is alkoxy, halo or alkynyl. Preferably R$^2$ is alkoxy.

In certain embodiments of formula q1, R$^2$ and R$^3$ are hydrogen and R$^1$ is alkoxy, halo or alkynyl. Preferably R$^1$ is alkoxy.

In certain embodiments of formula q1, R$^4$ is methyl.

The invention also provides compounds of formula q2

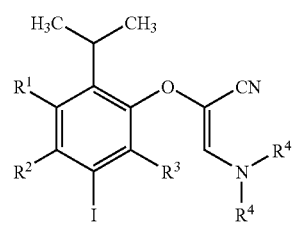

or salts thereof, wherein:

R$^1$, R$^2$ and R$^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH$_2$)$_m$—(Z)$_n$—(CO)—R$^f$ or —(CH$_2$)$_m$—(Z)$_n$—SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or R$^2$ and R$^3$ together with the atoms to which they are attached may form a five or six-membered ring that optionally includes one or two heteroatoms selected from O, S and N; and R$^4$ is alkyl.

In certain embodiments of formula q2, R$^1$ and R$^3$ are hydrogen and R$^2$ is alkoxy, halo or alkynyl. Preferably R$^2$ is alkoxy.

In certain embodiments of formula q2, R$^2$ and R$^3$ are hydrogen and R$^1$ is alkoxy, halo or alkynyl. Preferably R$^1$ is alkoxy.

In certain embodiments of formula q2, R$^4$ is methyl.

The invention also provides a composition comprising a compound of formula q1, a compound of formula q2, or a mixture thereof,

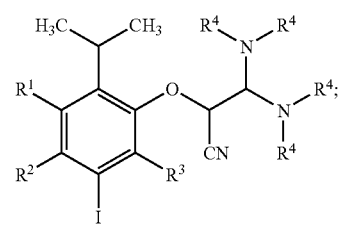

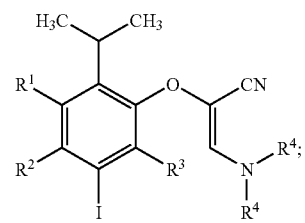

or salts thereof, in admixture with a polar aprotic solvent, wherein:

R$^1$, R$^2$ and R$^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH$_2$)$_m$—(Z)$_n$—(CO)—R$^f$ or —(CH$_2$)$_m$—(Z)$_n$—SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or R$^2$ and R$^3$ together with the atoms to which they are attached may form a five or six-membered ring that optionally includes one or two heteroatoms selected from O, S and N; and R$^4$ is alkyl.

The invention also provides compounds of formula p

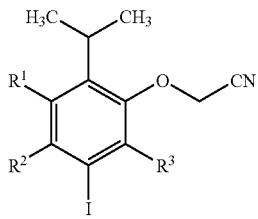

or salts thereof, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_m$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments of formula p, $R^1$ and $R^3$ are hydrogen and $R^2$ is alkoxy, halo or alkynyl. Preferably $R^2$ is alkoxy.

In certain embodiments of formula p, $R^2$ and $R^3$ are hydrogen and $R^1$ is alkoxy, halo or alkynyl. Preferably R1 is alkoxy.

The invention also provides compounds of formula o

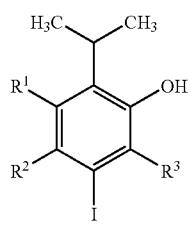

or salts thereof, wherein:

$R^1$, $R^2$ and $R^3$ each independently is: hydrogen; alkyl; alkenyl; alkynyl, amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$—$(Z)_n$—(CO)—$R^f$ or —$(CH_2)_n$—$(Z)_n$—$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^2$ and $R^3$ together with the atoms to which they are attached may form a five or six-membered ring that optionally includes one or two heteroatoms selected from O, S and N.

In certain embodiments of formula o, $R^1$ and $R^3$ are hydrogen and $R^2$ is alkoxy, halo or alkynyl. Preferably $R^2$ is alkoxy.

In certain embodiments of formula o, $R^2$ and $R^3$ are hydrogen and $R^1$ is alkoxy, halo or alkynyl. Preferably R1 is alkoxy.

Where any of $R^1$, $R^2$, $R^3$, $R^4$ or $R^5$ is alkyl or contains an alkyl moiety, such alkyl is preferably lower alkyl, i.e. $C_1$-$C_6$alkyl, and more preferably $C_1$-$C_4$alkyl.

Specific details for the methods of the invention are described in the Examples section below.

Utility

The methods and compounds of the invention are useful for preparation of compounds that in turn are usable for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The methods and compounds of the invention are useful for preparation of compounds that in turn are usable for the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

The methods and compounds of the invention are useful for preparation of compounds that in turn are usable for treating respiratory disorders, including chronic obstructive pulmonary disorder (COPD), asthma, bronchospasm, and the like.

Additionally, methods and compounds of the invention are useful for preparing compounds for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

The compounds of the invention in particular find industrial application as intermediates in the synthesis of compounds useful for the above treatments.

EXAMPLES

The following preparations and examples are given to enable those skilled in the art to more clearly understand and to practice the present invention. They should not be considered as limiting the scope of the invention, but merely as being illustrative and representative thereof.

Example 1

5-(5-Iodo-2-isopropyl-4-methoxy-phenoxy)-pyrimidine-2,4-diamine

The synthetic procedure used in this Example is outlined in Scheme D.

SCHEME D

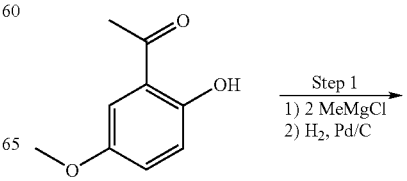

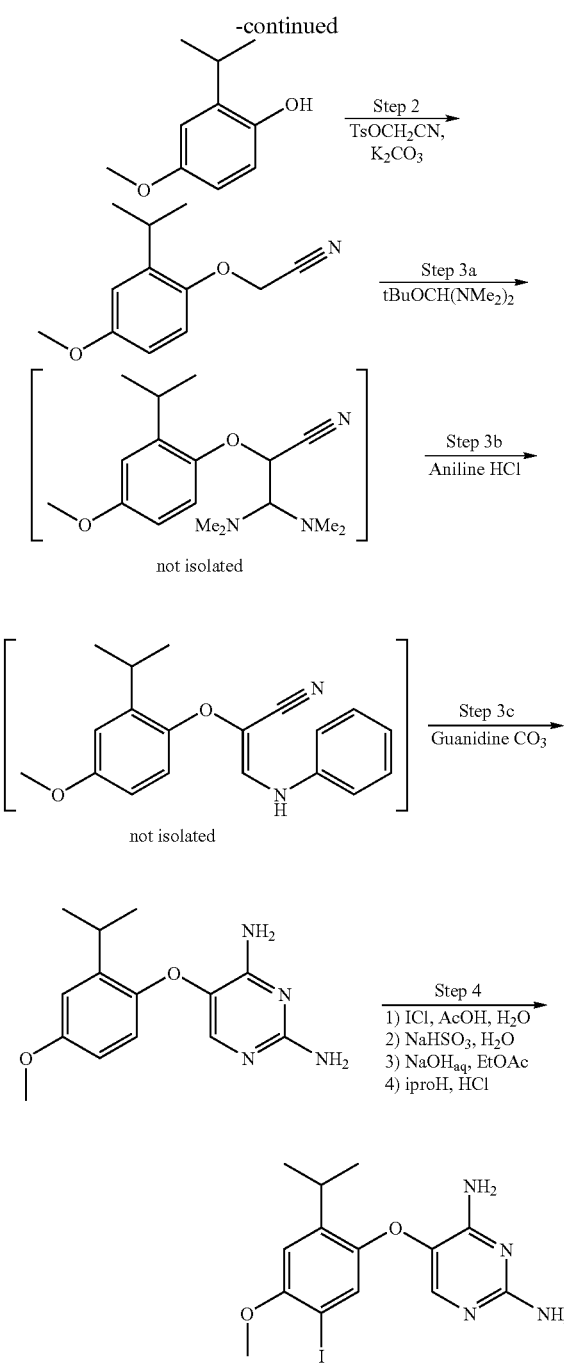

not isolated not isolated

Step 1 2-Isopropyl-4-methoxy-phenol

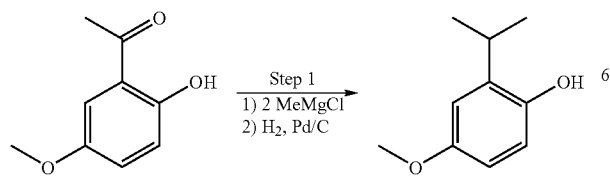

To a cooled solution of 1-(2-hydroxy-5-methoxy-phenyl)-ethanone (10.0 kg) in 79.0 kg of THF was gradually added 46.4 kg of 3M solution of MeMgCl in THF at a rate such that the reaction mixture temperature did not exceed 25 degrees C. Following addition of the MeMgCl solution, the reaction mixture was stirred at ambient temperature for 18 hours, at which point HPLC analysis showed more than 98% conversion of 1-(2-hydroxy-5-methoxy-phenyl)-ethanone to 2-(1-hydroxy-1-methyl-ethyl)-4-methoxy-phenol (not shown in Scheme D). To the stirred solution was then added 10% palladium on carbon (1.02 kg, 50% water wet) suspended in 3.5 Kg of THF. The reaction mixture was cooled and placed under a hydrogen atmosphere at 5 psig, and concentrated HCl (19.5 kg) was added while maintaining the reaction temperature at 25° C. The resultant mixture was stirred at ambient temperature for 18 hours, then treated with 44.4 kg water and filtered through a bed of Celite to remove suspended catalyst. The filter cake was rinsed with EtOAc and the combined filtrate was separated. The organic phase was washed with water, then concentrated by distillation to provide an oil. This oil was dissolved in 2-butanone (20.4 kg) and the crude solution was employed directly in the next step. A 161.8 g aliquot of the solution was concentrated under vacuum to provide 49.5 g of 2-isopropyl-4-methoxyphenol as an oil, projecting to 10.4 kg crude contained product in the bulk 2-butanone solution. $^1$H nmr (DMSO) delta: 1.14 (d, 6H, J=6.9 Hz), 3.18 (septet, 1H, J=6.9 Hz), 3.65 (s, 3H), 6.56, (dd, 1H, J=8.6 Hz, 3.1 Hz), 6.67 (d, 1H, J=3.1 Hz), 6.69 (d, 1H, 8.6 Hz).

Step 2 (2-Isopropyl-4-methoxy-phenoxy)-acetonitrile

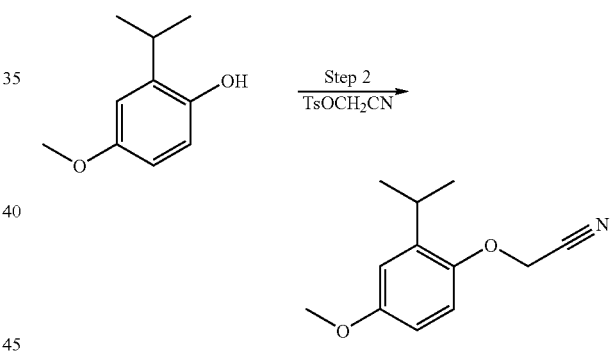

A stirred slurry of toluene-4-sulfonic acid cyanomethyl ester (13.0 kg), potassium carbonate (13.0 kg) and 2-isopropyl-4-methoxyphenol (9.57 Kg) in 79.7 kg of 2-butanone was heated to 55-60 degrees C. for 4 days, then heated to reflux for 18 hours. The resultant slurry was cooled and filtered to remove solids. The filtrate was concentrated under reduced pressure and the residue was redissolved in toluene. The toluene solution was extracted with 1N KOH, and the organic phase was concentrated by distillation to give 20.6 g of a 1:1 (by weight) solution of (2-Isopropyl-4-methoxy-phenoxy)-acetonitrile in toluene, which was used directly in the next step. A anliquot (96.7 g) of this solution was concentrated to dryness to give 50.9 g of crude (2-Isopropyl-4-methoxy-phenoxy)-acetonitrile, projecting to a yield of 10.9 kg in the bulk solution: MS (M+H)=206; $^1$H nmr (CDCl$_3$) delta: 1.25 (d, J=6.9 Hz), 3.31 (septet, 1H, J=6.9 Hz), 3.82 (s, 3H), 4.76 (s, 2H), 6.73 (dd. $^1$H, J=8.8 Hz, 3.1 Hz), 6.87 (d, 1H, J=3.1 Hz), 6.91 (d, 1H, J=8.8 Hz)

Step 3  5-(2-Isopropyl-4-methoxy-phenoxy)-pyrimidine-2,4-diamine

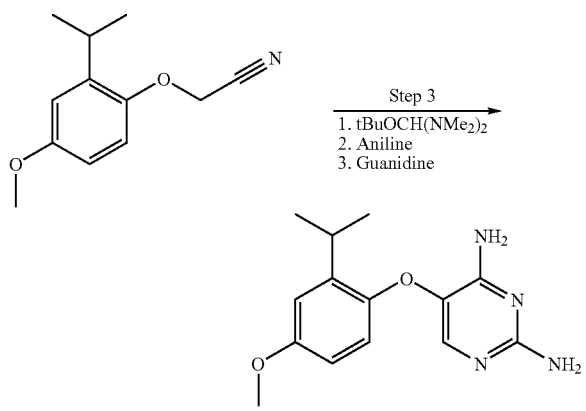

Step 4  5-(5-Iodo-2-isopropyl-4-methoxy-phenoxy)-pyrimidine-2,4-diamine

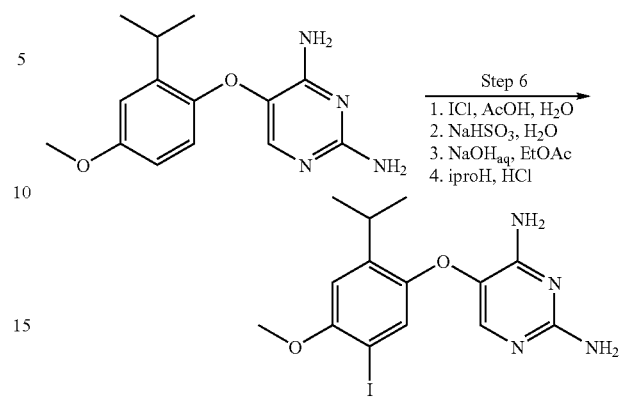

An approximately 1:1 (by weight) solution of 10.6 kg of (2-Isopropyl-4-methoxy-phenoxy)-acetonitrile in toluene was concentrated under reduced pressure and the residue was treated with 10.8 kg of tert-butoxybis(dimethylamino)methane (Brederick's Reagent). The resulting mixture was dissolved in 20.2 kg of DMF and the solution was heated to 110 degrees C. for 2 hours, at which point HPLC analysis showed essentially complete conversion to 3,3-Bis-dimethylamino-2-(2-isopropyl-4-methoxy-phenoxy)-propionitrile (not isolated, $^1$H nmr (CDCl$_3$) delta: 1.21 (d, 3H, J=7.2 Hz), 1.23 (d, 3H, J=7.1 Hz), 2.46 (s, 6H), 2.48 (s, 6H), 3.43 (d, 1H, J=5.0 Hz), 3.31 (septet, 1H, J=6.9 Hz), 3.79 (s, 3H), 4.93 (d, 1H, J=5.0 Hz), 6.70 (dd, 1H, J=8.8 Hz, 3.0 Hz), 6.82 (d, 1H, J=3.0 Hz), 6.98 (d, 1H, J=8.8 Hz).

The DMF solution was cooled and transferred onto 14.7 kg of aniline hydrochloride. The resulting mixture was heated to 120 degrees C. for 22 hours, at which point HPLC analysis showed greater than 97% conversion to 2-(2-Isopropyl-4-methoxy-phenoxy)-3-phenylamino-acrylonitrile (not isolated, $^1$H nmr (CDCl$_3$) delta: 1.31 (d, 6H, J=6.9 Hz), 3.39 (septet, 1H, J=6.9 Hz), 3.82 (s, 3H), 6.61 (d (br), 1H, J=12.7 Hz), 6.73 (dd, 1H, J=8.9 Hz, 3.1 Hz), 6.88 (d, 1H, J=3.0 Hz), 6.93 (m, 2H), 6.97 (d, 1H, J=8.9 Hz), 7.05 (m, 1H), 7.17 (d, 1H, J=12.6 Hz), 7.35 (m. 2H)).

The mixture was cooled, diluted with 21.5 kg toluene, then with 72.2 L of water. The organic layer was separated, washed with water, and concentrated by distillation. The concentrate was transferred into 23.8 kg DMF, and the DMF solution was transferred onto 6.01 kg of guanidine carbonate. The resulting mixture was heated to 120 degrees C. for 3 days, at which point HPLC analysis showed greater than 95% conversion of 2-(2-Isopropyl-4-methoxy-phenoxy)-3-phenylamino-acrylonitrile into 5-(2-Isopropyl-4-methoxy-phenoxy)-pyrimidine-2,4-diamine.

The reaction mixture was cooled, diluted with 7.8 kg of EtOAc, then reheated to 60 degrees C. Water (75.1 L) was added and the resultant mixture was allowed to cool to ambient temperature. The precipitated solid was collected by filtration, rinsed with isopropanol and dried under vacuum at 50 degrees to give 9.62 kg of 5-(2-isopropyl-4-methoxy-phenoxy)-pyrimidine-2,4-diamine: m.p. 170-171 degrees C.; MS (M+H)=275; $^1$H nmr (chloroform) delta: 1.25 (d, 6H, J=6.9 Hz), 3.30 (septet, 1H, J=6.9 Hz), 3.79 (s, 3H), 4.68 (br, 2H), 4.96 (br, 2H), 6.64 (dd, 1H, J=8.9 Hz, 3.0 Hz), 6.73, d, J=8.9 Hz), 6.85 (d, 1H, J=3 Hz), 7.47 (s, 1H).

To a solution of 5-(2-isopropyl-4-methoxy-phenoxy)-pyrimidine-2,4-diamine (6.50 kg) in mL acetic acid was added a solution of 9.205 kg ICl (iodine monochloride) in 7.5 kg of acetic acid, with addition carried out at a rate such that the temperature of the resulting mixture did not exceed 24 degrees C. Water (11.0 kg) was added and the resultant mixture was stirred at 25 degrees C. for 42 hours, at which point HPLC analysis showed greater than 95% conversion of 5-(2-isopropyl-4-methoxy-phenoxy)-pyrimidine-2,4-diamine to 5-(5-Iodo-2-isopropyl-4-methoxy-phenoxy)-pyrimidine-2,4-diamine.

Excess ICl was decomposed by the addition of aqueous solution of sodium bisulfite (3.505 kg) at a rate such that the temperature of the reaction mixture did not exceed 20 degrees C. Water (40 L) was added, and the resulting precipitate (a mixture of chloride, iodide and bisulfate salts) was collected by filtration and air-dried to give 8.86 kg of crude 5-(5-iodo-2-isopropyl-4-methoxy-phenoxy)-pyrimidine-2,4-diamine salts. A suspension of the crude product in 90.7 kg water was made basic by addition of 50% NaOH, and the resulting solution was extracted into warm EtOAc. The combined organic layers were filtered and EtOAc was replaced by isopropanol via distillation. To the hot isopropanol solution was added 3.4 L of 6N HCl, and the resultant mixture was cooled slowly to 15 degrees C. Crystals of the resulting HCl salt were isolated by filtration, rinsed with isopropanol, and dried under vacuum at 70 degrees C. to give 6.08 kg (58.8%) of 5-(5-iodo-2-isopropyl-4-methoxy-phenoxy)-pyrimidine-2,4-diamine hydrochloride salt: m.p.=262.0-263.0° C.; MS (M+H)=401; $^1$H nmr (methanol) delta: 1.25 (d, 6H, J=6.9 Hz), 3.12 (septet. $^1$H, J=6.9 Hz), 3.89 (s, 3H), 4.85 (br), 6.91 (s, 1H), 6.94 (s, 1H), 7.45 (s, 1H).

Example 2

5-(5-Iodo-2-isopropyl-4-methoxy-phenoxy)-pyrimidine-2,4-diamine

The synthetic procedure used in this Example is outlined in Scheme D.

Scheme E

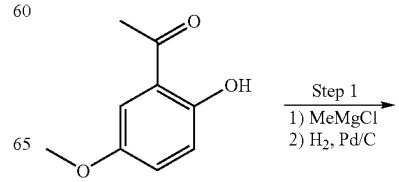

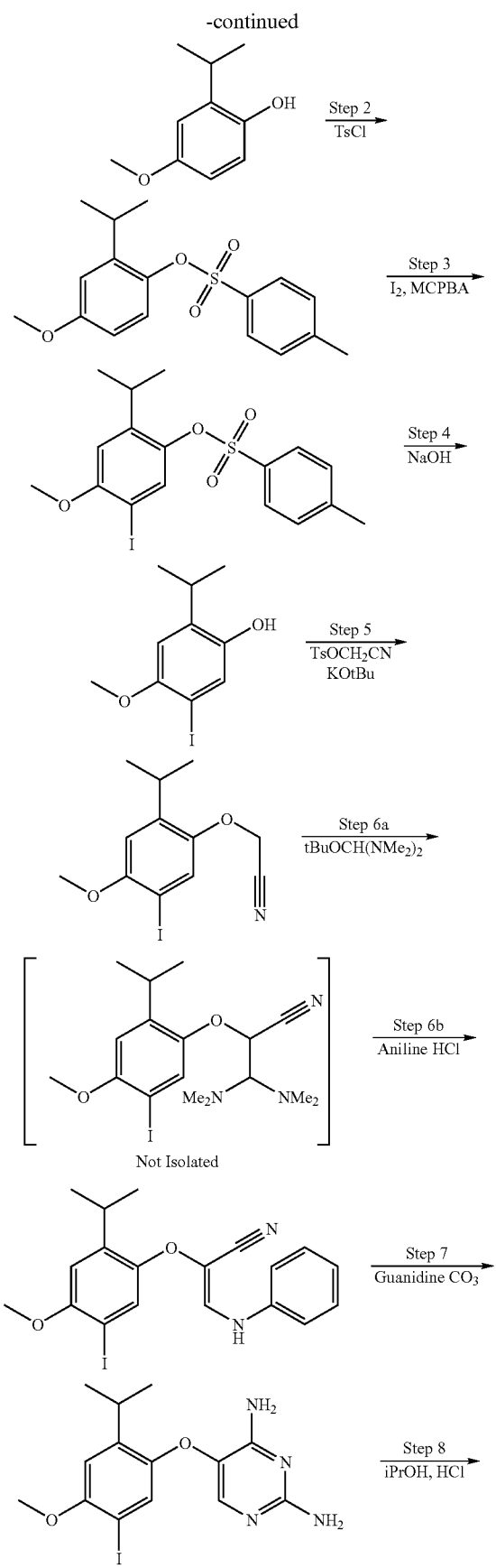

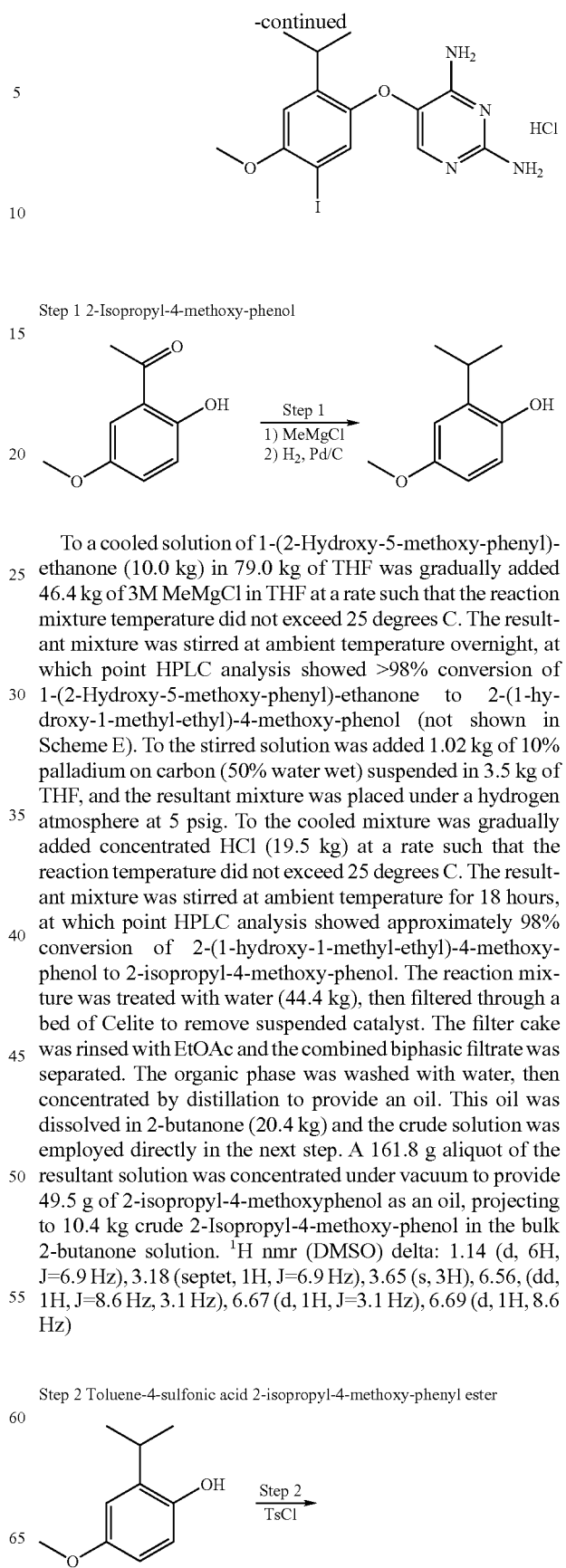

Step 1 2-Isopropyl-4-methoxy-phenol

To a cooled solution of 1-(2-Hydroxy-5-methoxy-phenyl)-ethanone (10.0 kg) in 79.0 kg of THF was gradually added 46.4 kg of 3M MeMgCl in THF at a rate such that the reaction mixture temperature did not exceed 25 degrees C. The resultant mixture was stirred at ambient temperature overnight, at which point HPLC analysis showed >98% conversion of 1-(2-Hydroxy-5-methoxy-phenyl)-ethanone to 2-(1-hydroxy-1-methyl-ethyl)-4-methoxy-phenol (not shown in Scheme E). To the stirred solution was added 1.02 kg of 10% palladium on carbon (50% water wet) suspended in 3.5 kg of THF, and the resultant mixture was placed under a hydrogen atmosphere at 5 psig. To the cooled mixture was gradually added concentrated HCl (19.5 kg) at a rate such that the reaction temperature did not exceed 25 degrees C. The resultant mixture was stirred at ambient temperature for 18 hours, at which point HPLC analysis showed approximately 98% conversion of 2-(1-hydroxy-1-methyl-ethyl)-4-methoxy-phenol to 2-isopropyl-4-methoxy-phenol. The reaction mixture was treated with water (44.4 kg), then filtered through a bed of Celite to remove suspended catalyst. The filter cake was rinsed with EtOAc and the combined biphasic filtrate was separated. The organic phase was washed with water, then concentrated by distillation to provide an oil. This oil was dissolved in 2-butanone (20.4 kg) and the crude solution was employed directly in the next step. A 161.8 g aliquot of the resultant solution was concentrated under vacuum to provide 49.5 g of 2-isopropyl-4-methoxyphenol as an oil, projecting to 10.4 kg crude 2-Isopropyl-4-methoxy-phenol in the bulk 2-butanone solution. $^1$H nmr (DMSO) delta: 1.14 (d, 6H, J=6.9 Hz), 3.18 (septet, 1H, J=6.9 Hz), 3.65 (s, 3H), 6.56, (dd, 1H, J=8.6 Hz, 3.1 Hz), 6.67 (d, 1H, J=3.1 Hz), 6.69 (d, 1H, 8.6 Hz)

Step 2 Toluene-4-sulfonic acid 2-isopropyl-4-methoxy-phenyl ester

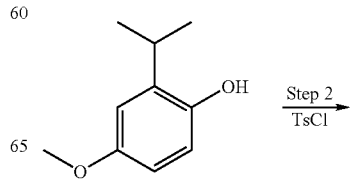

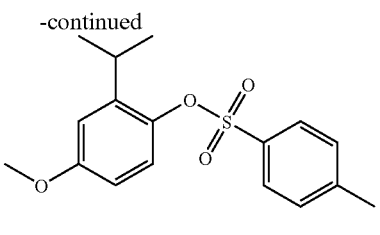

To a solution of 180 g of 2-Isopropyl-4-methoxy-phenol (1.084 moles) in 2.5 L toluene was added 206.7 g p-toluene sulfonylchloride (1.084 moles), and the reaction mixture was stirred vigorously The resultant mixture was cooled to 10° C., and triethylamine (3 mol) was gradually added, keeping the temperature below 50 degrees C. The reaction mixture was aged for 3 hours at approximately 50° C. and then allowed to cool to RT. An HPLC sample obtained at this point showed completion of the reaction. The resultant suspension was filtered and the filter-cake was washed with 300 mL toluene. The collected filtrate was distilled under vacuum until the pot-temperature reached 65° C., and 1 L of methanol was added to the mixture. The methanolic solution was stirred for 30 minutes at reflux; then the mixture was permitted to cool overnight. The white crystalline solid which separated was collected by filtration and dried at 50° C. under vacuum to yield a total of 332 grams of toluene-4-sulfonic acid 2-isopropyl-4-methoxy-phenyl ester, representing an yield of 95.7%:m.p. 85.1 degrees C.

Step 3 Toluene-4-sulfonic acid 5-iodo-2-isopropyl-4-methoxy-phenyl ester

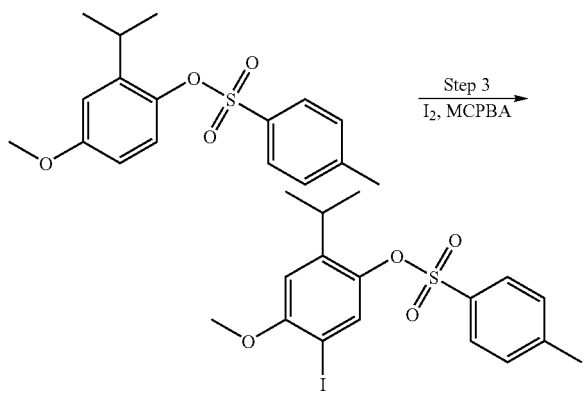

To a solution of 282 grams of toluene-4-sulfonic acid 2-isopropyl-4-methoxy-phenyl ester (0.88 Moles) in 900 mL acetic acid was gradually added 111.5 grams of iodine (0.44 moles). To the resultant mixture was added, over a period of 6 hours, a slurry of 224 grams meta-chloro perbenzoic acid (mCPBA, 1.14 moles) in 400 mL ethyl acetate. The reaction mixture was stirred at ambient temperature for 16 hours and then analyzed by HPLC, which showed complete conversion of toluene-4-sulfonic acid 2-isopropyl-4-methoxy-phenyl ester to toluene-4-sulfonic acid 5-iodo-2-isopropyl-4-methoxy-phenyl ester. The product suspension was filtered, and the solid product was washed with water; then dried under vacuum at 65 degrees C. overnight to give 292 grams of toluene-4-sulfonic acid 5-iodo-2-isopropyl-4-methoxy-phenyl ester, representing a yield of 74.5%.

Step 4 5-Iodo-2-isopropyl-4-methoxy-phenol

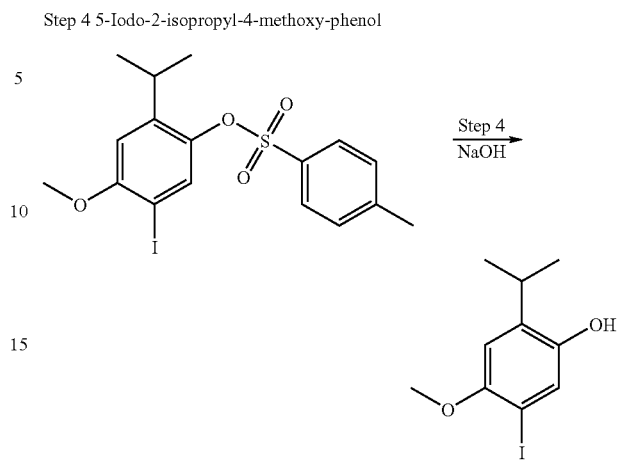

To a mixture of 292 grams of toluene-4-sulfonic acid 5-iodo-2-isopropyl-4-methoxy-phenyl ester (0.66 Moles) in 600 mL tert-butyl alcohol was gradually added a solution of 90 g KOH in 400 mL water, and the resultant mixture was stirred overnight at 82 degrees C. The reaction mixture was neutralized with conc. HCl to a pH of 5-6, and then partitioned between 600 mL ethyl acetate and 400 mL water. The organic phase was dried over sodium sulfate, filtered and stripped under vacuum at 65 degrees C. to give a resinous liquid. Hexane (700 mL) was then added and the mixture heated to reflux. The liquid phase was decanted into another flask and stirred overnight at room temperature, during which time a white solid precipitated. The solid was isolated by filtration and vacuum dried to give 162 g of 5-iodo-2-isopropyl-4-methoxy-phenol, representing a yield of 82%: MS (M+H)=293.

Step 5 (5-Iodo-2-isopropyl-4-methoxy-phenoxy)-acetonitrile

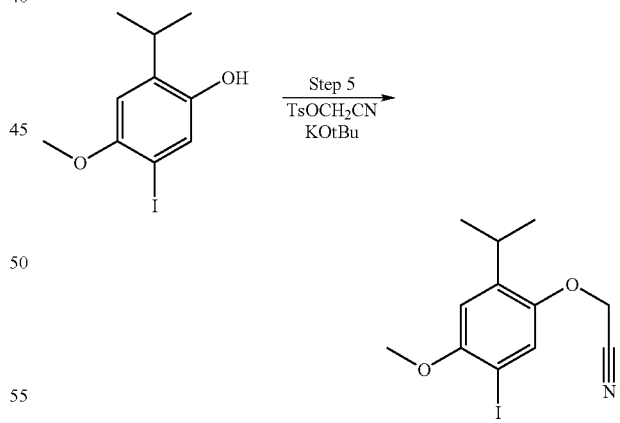

To a cold (1 degree C.) solution of 10.0 g of 5-iodo-2-isopropyl-4-methoxy-phenol in 25 mL THF was added 41.3 mL of 1N KOtBu in THF at a rate such that the internal temperature did not exceed 6 degrees C. To the resultant phenoxide solution was added a solution of 7.2 g of toluene-4-sulfonic acid cyanomethyl ester in 25 mL THF, and the reaction mixture was allowed to warm slowly to ambient temperature overnight. The reaction mixture was partitioned between n-heptane (50 mL) and water (50 mL), and the organic layer was displaced into n-heptane by distillation (to a pot temperature of 97 degrees C.). The concentrate in n-heptane was cooled slowly to ambient temperature and the resulting crystalline solid was washed with n-heptane and dried. In this manner, 9.26 g of (5-iodo-2-isopropyl-4-methoxy-phenoxy)-acetonitrile was isolated (81%): m.p. 67.5-68.8 degrees C.; $^1$H nmr (DMSO) delta: 1.18 (d, 6H, J=6.9 Hz), 3.19 (septet, 1H, J=6.9 Hz), 3.81 (s, 3H), 5.16 (s 2H), 6.88 (s, 1H), 7.50 (s, 1H).

Step 6 2-(5-Iodo-2-isopropyl-4-methoxy-phenoxy)-3-phenylamino-acrylonitrile

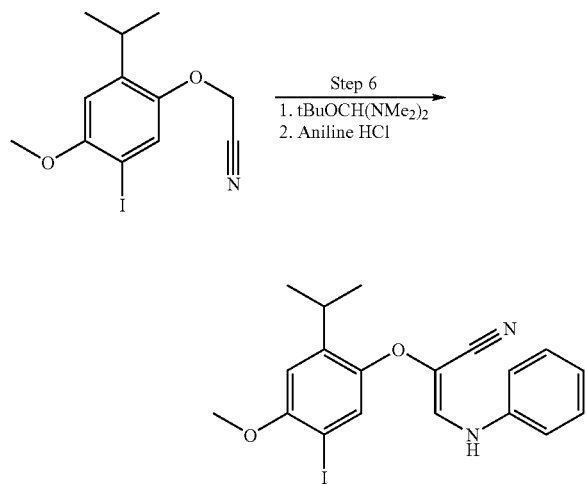

To a solution of (5-iodo-2-isopropyl-4-methoxy-phenoxy)-acetonitrile (250 g, 0.75 mol) in 500 ml of DMF, t-butoxybis(dimethylamino)methane (167 g, 0.96 mol) was added. The mixture was heated to 100° C. for 4 hours, then cooled to 25° C. to provide a DMF solution of 3,3-bis-dimethylamino-2-(5-iodo-2-isopropyl-4-methoxy-phenoxy)-propionitrile (not isolated). To this solution was added aniline hydrochloride (225 g, 1.7 mol), and the resultant mixture was heated to 100° C. for 11 hours. After cooling to 60° C., 100 ml of isopropanol was added, followed by 1 L of water, at a rate to maintain an internal temperature of 50° C. The resulting slurry was cooled to 20° C. and aged. Precipitated 2-(5-Iodo-2-isopropyl-4-methoxy-phenoxy)-3-phenylamino-acrylonitrile was collected by filtration, washed with isopropanol until the filtrate was colorless, and dried in a vacuum oven (50° C., 24 inches Hg) to give 310 g of 2-(5-Iodo-2-isopropyl-4-methoxy-phenoxy)-3-phenylamino-acrylonitrile, 93% yield: Melting Point: 170° C.; $^1$HNMR (CDCl$_3$) δ=1.3 (d, 6H), 3.3 (m, 1H), 3.85 (s, 3H), 6.6 (d, 2H), 6.75 (s, 1H), 6.9 (d, 2H), 7.05 (t, 1H), 7.15 (d, 1H), 7.3 (t, 3H)

Step 7 5-(5-Iodo-2-isopropyl-4-methoxy-phenoxy)-pyrimidine-2,4-diamine

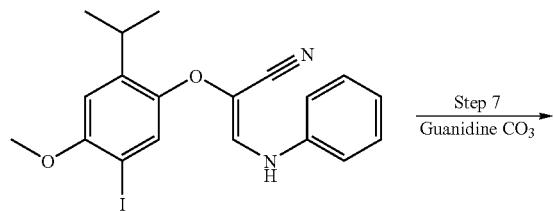

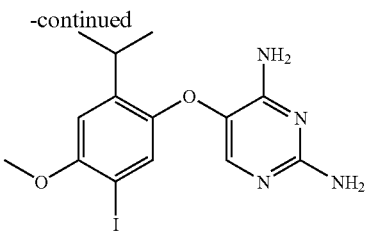

A solution of 2-(5-iodo-2-isopropyl-4-methoxy-phenoxy)-3-phenylamino-acrylonitrile (280 g, 0.64 mol), guanidine carbonate (110 g, 0.61 mol), and 560 ml of DMF was heated to 120° C. for 18 hours. After cooling the mixture to 60° C., 140 ml of ethyl acetate was added. Water (1.12 L) was then added to the mixture at a rate to maintain an internal temperature of 50° C. The resulting slurry was cooled to 20° C. and aged. Precipitated solids were collected by filtration, washed with water (300 ml) followed by isopropanol (500 ml), and dried in a vacuum oven (50° C., 24 inches Hg) to give 242 g of 5-(5-iodo-2-isopropyl-4-methoxy-phenoxy)-pyrimidine-2,4-diamine, 94% yield: m.p. 204.4-205.9 degrees C.; $^1$HNMR (DMSO) δ=1.2 (d, 6H), 3.3 (m, 1H), 3.8 (s, 3H), 5.85 (s, 2H), 6.4 (s, 2H), 6.9 (d, 2H), 7.35 (s, 1H)

Step 8 5-(5-Iodo-2-isopropyl-4-methoxy-phenoxy)-pyrimidine-2,4-diamine Hydrochloride Salt.

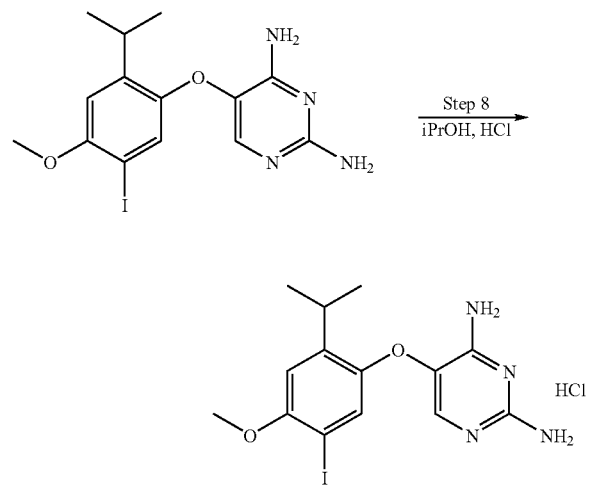

5-(5-Iodo-2-isopropyl-4-methoxy-phenoxy)-pyrimidine-2,4-diamine A mixture of 5-(5-iodo-2-isopropyl-4-methoxy-phenoxy)-pyrimidine-2,4-diamine (240 g, 0.60 mol) in 1.2 L of isopropanol was heated to 70° C. An aqueous solution of 6N HCl was added dropwise to the reaction mixture, and the slurry was heated to 75° C. for two hours. The slurry was cooled to 20° C. and aged. Precipitated solids were collected by filtration, washed with cold isopropanol, and dried in a vacuum oven (50° C., 24 inches Hg) to give 232 g of -(5-iodo-2-isopropyl-4-methoxy-phenoxy)-pyrimidine-2,4-diamine hydrochloride salt, 98% yield: m.p. 262.0-263.0 degrees C.; $^1$HNMR (DMSO) δ=1.2 (d, 6H), 3.1 (m, 1H), 3.85 (s, 3H), 6.95 (s, 1H), 7.25 (s, 1H), 7.45 (s, 1H), 7.6 (s, 2H), 8.25 (s, 1H), 8.6 (s, 1H), 11.9 (s, 1H).

Example 3

P2X$_3$/P2X$_{2/3}$ FLIPR (Fluorometric Imaging Plate Reader) Assay

CHO-K1 cells were transfected with cloned rat P2X$_3$ or human P2X$_{2/3}$ receptor subunits and passaged in flasks. 18-24 hours before the FLIPR experiment, cells were released from their flasks, centrifuged, and resuspended in nutrient medium at 2.5×10$^5$ cells/ml. The cells were aliquoted into black-walled 96-well plates at a density of 50,000 cells/well and incubated overnight in 5% CO$_2$ at 37° C. On the day of the experiment, cells were washed in FLIPR buffer (calcium- and magnesium-free Hank's balanced salt solution, 10 mM HEPES, 2 mM CaCl$_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well agonist or vehicle addition. The agonist was a 2× solution of α,β-meATP producing a final concentration of 1 µM (P2X$_3$) or 5 µM (P2X$_{2/3}$). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the P2X$_3$ receptor. Using the above assay, the compound 5-(5-iodo-2-isopropyl-4-methoxy-phenoxy)-pyrimidine-2,4-diamine exhibited a pIC$_{50}$ of approximately 8.0 for the P2X$_3$ receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for preparing a compound of formula I

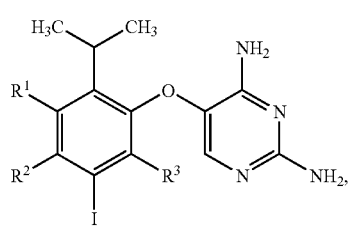

the method comprising:

treating a compound of formula h

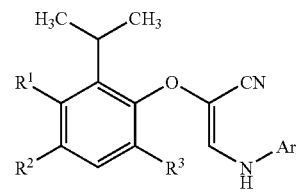

with a guanidine regent, to form a compound of formula d

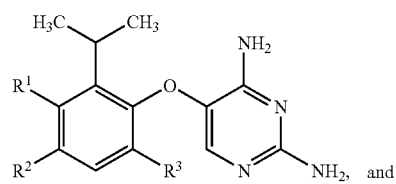

treating the compound of formula d with an iodination reagent, to form the compound of formula I, wherein:

R$^1$ and R$^3$ are hydrogen; and

R$^2$ is methoxy.

2. The method of claim 1, wherein the iodination reagent is iodine monochloride.

3. The method of claim 1, wherein the compound of formula d is dissolved or partly dissolved in acetic acid or a mixture of acetic acid and water.

4. The method of claim 1, wherein the guanidine reagent is guanidine carbonate.

5. The method of claim 1, further comprising treating a compound of formula g1, formula g2, or a mixture thereof,

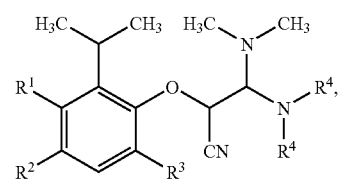

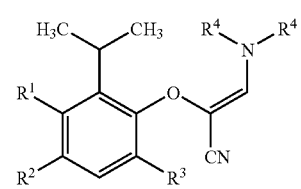

wherein Ar, R$^1$, R$^2$, R$^3$ are as defined herein and R$^4$ is alkyl, with an aniline reagent, to form the compound of formula h.

6. The method of claim 5, further comprising treating a compound of formula c

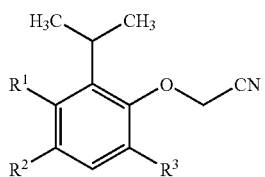

c wherein Ar, R¹, R² and R³ are as defined herein,
with Brederick's reagent, to form said compound of formula g1, or formula g2, or the mixture thereof.

7. The method of claim 6, further comprising treating a compound of formula b

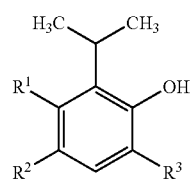

b wherein Ar, R¹, R² and R³ are as defined herein,
with cyanomethyl alkylating agent, to form the compound of formula c.

8. The method of claim 7, further comprising treating a compound of formula a

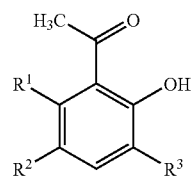

a wherein Ar, R¹, R² and R³ are as defined herein,
with methylmagnesium halide, followed by hydrogen in the presence of a hydrogenation catalyst and acid, to form said compound of formula b.

* * * * *